(12) United States Patent
Yamashiro (10) Patent No.: US 10,195,454 B2
(45) Date of Patent: Feb. 5, 2019

(54) USE OF MAGNETIC STIMULATION TO MODULATE MUSCLE CONTRACTION

(71) Applicant: Patsy Yamashiro, Anaheim, CA (US)

(72) Inventor: Patsy Yamashiro, Anaheim, CA (US)

(*) Notice: Subject to any disclaimer, the term of this patent is extended or adjusted under 35 U.S.C. 154(b) by 0 days.

(21) Appl. No.: 14/545,427

(22) Filed: May 4, 2015

(65) Prior Publication Data

US 2015/0314133 A1 Nov. 5, 2015

Related U.S. Application Data

(60) Provisional application No. 61/996,302, filed on May 5, 2014.

(51) Int. Cl.
| | |
|---|---|
| *A61N 2/00* | (2006.01) |
| *A61N 2/02* | (2006.01) |
| *A61N 5/06* | (2006.01) |
| *A61N 1/36* | (2006.01) |

(52) U.S. Cl.
CPC ............ *A61N 2/006* (2013.01); *A61N 2/004* (2013.01); *A61N 1/3601* (2013.01); *A61N 1/36007* (2013.01); *A61N 2/02* (2013.01); *A61N 5/0622* (2013.01)

(58) Field of Classification Search
CPC ........ A61N 2/02; A61N 2/004; A61N 1/3601; A61N 5/0622; A61N 1/36007; A61N 2/006
USPC ................................ 600/9, 14; 128/897–899
See application file for complete search history.

(56) References Cited

U.S. PATENT DOCUMENTS

| | | | | |
|---|---|---|---|---|
| 6,520,903 B1* | 2/2003 | Yamashiro | ........... | A61N 5/0618 600/9 |
| 6,916,329 B1* | 7/2005 | Zhao | .................... | A61H 39/002 128/907 |
| 2005/0070977 A1* | 3/2005 | Molina | .................. | A61N 2/002 607/88 |
| 2006/0106434 A1* | 5/2006 | Padgitt | ..................... | A61N 1/32 607/66 |
| 2007/0005119 A1* | 1/2007 | Crohn | .................... | A61H 39/08 607/88 |
| 2011/0125203 A1* | 5/2011 | Simon | ...................... | A61N 1/40 607/2 |

OTHER PUBLICATIONS

Grishin, S. et al. Neurochemistry Int 49: 756-763, 2006.
Linden, A. et al. Br J Pharmacol 104: 509-513, 1991.
Miura, M. and J. Okada J Physiol. 435: 257-273, 1991.

* cited by examiner

*Primary Examiner* — Navin Natnithithadha
*Assistant Examiner* — Sunita Reddy (57) ABSTRACT

The present invention describes methods and devices comprising magnetic, radio frequency burst, and light stimulation to modulate muscle contraction. The magnetic stimulation may be delivered to the muscle using one or more coils that is placed transcutaneously. The methods and devices are useful to treat a number of conditions or disease conditions, including for example, gastroesophageal cramps and sphincter leakage.

2 Claims, 11 Drawing Sheets

Control        Post magnetic
               stimulation

Control          During Magnetic
                 Stimulation

USE OF MAGNETIC STIMULATION TO MODULATE MUSCLE CONTRACTION

CROSS-REFERENCE TO RELATED PUBLICATIONS

This application claims priority under USC 119(e) of U.S. Provisional Application 61/996,302 filed May 5, 2014, which is incorporated by reference herein in its entirety

FEDERALLY SUPPORTED RESEARCH AND DEVELOPMENT

No federally supported research and development

REFERENCE TO COMPACT DISC OR STORED MEDIA

No compact disc or stored media referenced or submitted

FIELD OF INVENTION

This invention relates to the use of magnetic, radio frequency burst, and light stimulation to modulate muscle contraction.

BACKGROUND OF THE INVENTION

1. All references cited herein are incorporated by reference in their entirety as though fully set forth. Unless defined otherwise, technical and scientific terms used herein have the same meaning as commonly understood by one of ordinary skill in the art to which this invention belongs.

Clinical problems in muscle occur at the extremes of contraction. Painful excessive or continuous contractions (spasms or cramps) are common as well as inadequate contraction of gastrointestinal sphincters leading to undesireable leakage. Drug treatment typically target specific receptors such as acetylcholine(cholinergic), but due to the widespread location of such receptors in the body, have diverse side effects. Adverse side effects have made drug therapy ineffective for many. What is taught here is a non-drug method based on portable externally applied magnetic, radiofrequency burst, and light stimulation targeting non-cholinergic receptors to modulate gastrointestinal smooth muscle and other muscle contraction. Portability and external application makes targeting of specific body problem areas possible non-invasively. In this way adverse reactions due to secondary effects can be minimized. Contraction or relaxation can be promoted by adjusting stimulation parameters. One embodiment of the proposed new device is treatment of the gastrointestinal system, but similar clinical problems are faced in the lungs and airway and can be treated in a similar way. The main differences for the airways are the specific smooth muscle fiber types and primary focus on relaxation responses. Smooth muscle is also located in every blood vessel of the body including the heart and lungs so similar cardiovascular problems may also be targeted. Pulmonary hypertension results when lung blood vessels are excessively constricted which can lead to pulmonary edema and gas exchange problems. Stimulation as described herein targeting lung vascular smooth muscle relaxation could be used as treatment to reduce pulmonary artery pressure. By limiting the treatment area of the applied stimulation to the lungs, a general systemic blood pressure effect can be avoided. The unique advantage of external magnetic, radiofrequecy burst, and light stimulation for treatment of the lungs is the simultaneous improvement of ventilation (bronchodilation) and perfusion (vasodilation) together. It is well known that the ratio of ventilation and perfusion in the lungs correlates with gas exchange. The more uniformly matched ventilation is to perfusion the better the gas exchange. The current inventive device then offers a means of improvement of gas exchange in a diseased lung where non-uniformity of ventilation perfusion ratio is a problem. Such non-uniformity is known to those skilled in the art to be a major clinical cause of low blood oxygenation. The non-cholinergic non-adrenergic receptors (NANC) targeted by the inventive device stimulation include the purinergic receptors which are linked to adenosine triphosphate (ATP) release as well as nitrergic receptors linked to nitric oxide . ATP applied externally is known to both enhance (diaphragm) and reduce (limb muscle) contraction force of skeletal muscle. Specific possible applications of the current inventive device are the relaxation of a cramped limb skeletal muscle and enhancing muscle contraction of the diaphragm of a patient suffering from respiratory insufficiency. ATP and purinergic receptors have also been found previously to have significant effects on diverse body functions such as cardiac function and mucus production. Intravenous ATP can depress cardiac muscle electrical conduction for suppression of arrhythmias. Mucus production in the eye and airways can be increased by ATP. Inadequate mucus liquid production occurs in cystic fibrosis where mucus is too thick for adequate clearance and during dry eye. Thus the potential clinical applications of the current inventive device go well beyond the specific application examples presented here for smooth and skeletal muscle problems. In different prior examples of negative responses connected with ATP administration it is important to note that as shown specifically for smooth muscle in the example described later, the specific pattern of administration and strength of stimulation could possibly reverse the negative to a positive effect. Nitric oxide is a well known smooth muscle relaxant, but has also been identified as being responsible for the "off" contraction following electrical stimulation of smooth muscle. Nitric oxide during electrical stimulation is known to cause a significant relaxation response especially in certain types of pre-contracted smooth muscle. Both purinergic and nitrergic receptors can be targeted by the current inventive device for specific applications.

The most common functional gastrointestinal problem is irritable bowel syndrome (IBS) which affects about 14% of the US population(Hungin 2005)). Abdominal pain and discomfort typically prompts consultation and drug therapy using antispasmotics or smooth muscle relaxants. Up to 68% of patients complained of side effects when given the high dose of antispasmotics required to improve pain (Lacy 2009). Thus, effectiveness of current therapy is limited. Antispasmotics affect cholinergic receptors which are present in all smooth muscle. Relaxing a contracted intestine can also relax sphincters and lead to undesirable leakage on either or both ends of the gastrointestinal tract.

Asthma affects about 8% of the US population and airway smooth muscle contraction leads to the need for treatment. Smooth muscle relaxants are used in treatment with a similar set of side effects as for gastrointestinal use. It should be emphasized that both constriction and dilation is possible by the inventive device stimulation and that only by careful adjustment of stimulation parameters can dilation be insured. Related to this is the known contraindication of administering intravenous ATP to asthmatics due to provoking possible bronchoconstriction. It is postulated that ATP can be involved in mediating bronchodilation as well, the pattern of stimulation leads to the difference in response.

Figure 1:
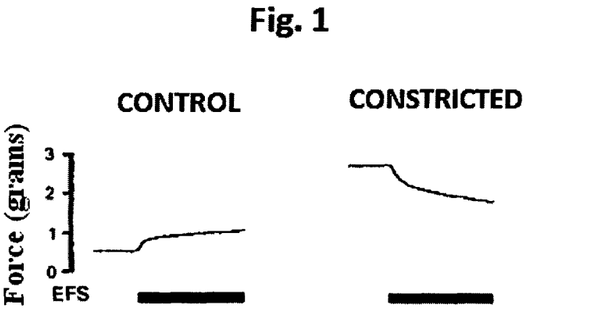
FIG. 1. Re-plotted data from (3) showing different effect of electrical stimulation before and following drug induced increase in resting tone in guinea pig airway smooth muscle with cholinergic block(atropine).

Electrical stimulation of the lower esophageal sphincter (LES) has been taught by Soffer and Conklin(U.S. Pat. No. 8,160,709) to modulate the contraction of this smooth muscle sphincter. The primary application was to treat gastrointestinal reflux disease (GERD) by applying a pulse train of electrical stimulation to promote sustained contraction. The treatment of smooth muscle spasm using different stimulation parameters was also taught. Electrical stimulation of circular esophageal smooth muscle fibers such as the LES which is already contracted is known by those skilled in the art to lead to relaxation during the period of stimulation. In fact, electrical stimulation of some types of smooth muscle is known to involve non-cholinergic non-adrenergic (NANC) receptors which can lead to contractile responses opposite to the pre-stimulation state (Linden 1991). Thus, a pre-contracted smooth muscle can relax and a relaxed muscle can contract. The mechanism leading to this difference in response is unclear, but may involve the smooth muscle actin-myosin directly. Stimulation of NANC receptors through nerves is also possible except that the stimulation threshold of the structures involved must be significantly lower. Because this is a critical observation concerning the current inventive strategy, the data of (Linden 1991) is re-plotted in FIG. 1. What is shown in FIG. 1 is the dependence of contraction or relaxation responses depending on the resting tone level. A relaxing response to electrical stimulation of the airway smooth muscle is observed when resting tension is high and a contracting response from a lower resting tension. It is important to note that the responses were limited to NANC receptors by a drug induced block of the cholinergic receptors present normally. Further support of a relaxation response is the finding that following histamine induced bronchoconstriction, direct vagal nerve stimulation does lead to bronchial relaxation in animals and NANC receptor participation in promoting relaxation was postulated(Hoffmann 2009). NANC mediated responses are sensitive to the level of contraction prior to stimulation as well as stimulation parameters. For stimulation applications for fixed locations, such as the LES, electrical stimulation using electrodes can be an effective means of therapy. However, the location of the specific part of the gastrointestinal system needing treatment is not always the same and can even change as a function of time. Use of electrical stimulation always requires specific positioning of electrodes which limits application. Invasive implantation of stimulation electrodes and associated electronics is also required which is a significant and costly barrier to more widespread use for therapy. Temporary application of trancutaneous(skin surface)electrical stimulation (TENS) is known to those skilled in the art to be problematic for this application due to lack of specificity of what is stimulated. Pain fiber stimulation typically limit stimulation level below effective levels Simon et al. (210130238049) proposed a transcutaneous electric nerve stimulator which was placed directly over the vagus nerve in the neck for stimulating vagus nerve afferent fibers for treatment of asthma. The relaxation of airway smooth muscle was the intended effect. Percutaneous (using needles through the skin) or direct electrical stimulation of the vagus nerve does lead to relaxation of airway smooth muscle as well as many other side effects since the vagus nerve affects most of the organs of the body. The most well known application of vagal stimulation is for epilepsy treatment. Obstructive sleep apnea has been reported as a major possible complication of this treatment. Transcutaneous stimulation level will always be limited by the pain produced by electrical current passing through the skin. So the effectiveness of this method is questionable and has yet to be shown.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are considered illustrative rather than restrictive.

DESCRIPTION OF THE INVENTION

What is proposed by one embodiment of the inventive device is the use of transcutaneous pulsed magnetic field for the purpose of stimulating NANC and other receptors to modulate muscle contraction. Magnetic stimulation as taught herein can be externally applied and used to treat internal body regions without pain fiber stimulation. It is important to note that magnetic stimulation as taught here specifically targets muscle and not the nerves which are connected to that muscle. This is the major difference from the prior art which for implanted electrical stimulation applications all target nerve stimulation exclusively. External application using a coil eliminates the requirement of a permanently fixed site of stimulation.

NANC receptor stimulation differs significantly from cholinergic "neural "transcutaneous pulsed magnetic field stimulation. Davy and Epstein(U.S. Pat. No. 5,725,471) have taught transcutaneous pulsed magnetic field neural stimulation for incontinence as well as skeletal muscle activation. One major difference for the present device is the required power level which is of the order of a factor of 10 less. Thus, cholinergic receptors will not be stimulated by the current inventive device which also minimizes the possible side effects and constitutes an advantage of this method. In fact, stimulation of cholinergic nerves would typically always lead to increased contraction by release of acetylcholine. This may be desireable for treatment of incontinence, but counterproductive for a cramp. A further advantage is the increased portability promoted by the lower power requirements. Transcutaneous pulsed magnetic nerve stimulators in general require high power and voltage in the kilovolts to operate. The 10 fold decrease in power makes conventional ac power voltages or even battery power possible to use without bulky transformers. The power requirements also led to a relatively high cost of purchase which further discouraged widespread use. Stimulation strategy is also different since many smooth muscle types do not show an all or none response resembling a nerve action potential. Instead, a pulse train using relatively narrow pulses and slow repetition frequencies of low power is used. An example of the use of the current inventive device for relaxing contracted pig esophageal smooth muscle is presented later. A magnetically induced voltage pulse of less than 3 volts was found to significantly reduce smooth muscle force for electrically induced prolonged contraction durations. This example shows for the first time the feasibility of modulating smooth muscle contraction using magnetic field stimulation without stimulating cholinergic nerves.

Another application of transcutaneous pulsed magnetic field is to stimulate bone growth or wound healing, such as taught by NASA (U.S. Pat. No. 7,601,114). This is a completely different application that most likely has nothing to do with NANC receptors and smooth muscle function. Stimulation parameters for this application are chosen more to generate a small continuous electric current which is felt to promote tissue healing. The level of induced current stimulation for tissue healing is lower than what is required to stimulate NANC receptors.

Transcutaneous pulsed magnetic field has also been used for tissue heating which is commonly called diathermy. NANC receptor stimulation as proposed by the present inventive device due to the low power applied is incapable of significantly changing tissue temperature so cannot be considered as related to diathermy.

Figure 2:
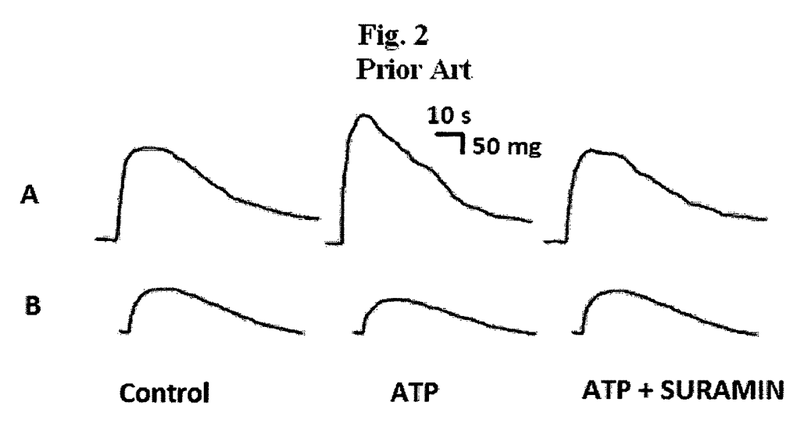
FIG. 2. From Grishin et al (6) A. Diaphragm B.Limb skeletal muscle.Suramin is an ATP receptor blocking agent.

Skeletal muscle cramps is a common problem with diverse causes. FIG. 2 shows the effect of ATP administration which has been previously reported (6) on contraction of two different types of skeletal muscle. The diaphragm (A) which is the main muscle of resting breathing increases contraction while limb muscle (B) decreases contraction. ATP release is an expected response to magnetic stimulation and radiofrequency burst as proposed herein. Thus, relaxation of a cramp contracted skeletal muscle is one of the useful applications of another embodiment of the inventive device. Many surgeries require cutting through muscle layers which often leads to cramping of the affected muscles. Muscle cramp relief following back and abdominal surgeries is an example of this application. ATP is known to be required during relaxation of a contracted muscle, so providing ATP during a state of deficiency would be expected to promote cramp relief.

Magnetic stimulation of the diaphragm could be used where augmentation of existing neural drive would be beneficial. For example, some of the nerve branches of the diaphragm could be damaged and uneven contraction could result. Applying magnetic stimulation synchronized to spontaneous breathing to the damaged area could improve contraction of the diaphragm and increase ventilation.

EXAMPLES

The following examples are provided to better illustrate the uses of the claimed invention and are not to be interpreted as limiting the scope of the invention. To the extent that specific materials are mentioned, it is merely for purposes of illustration and is not intended to limit the invention. One skilled in the art may develop equivalents without the exercise of inventive capacity and without departing from the scope of the invention.

The examples presented are based on pig esophageal smooth muscle which is considered to be close in properties to human esophagus. This tissue is made up of longitudinal and circular fibers very similar to the trachea and bronchi in arrangement and properties. This type of structure is also present throughout the gastrointestinal tract. There are functional differences, but responses to NANC receptor stimulation are largely consistent.

Figure 3:
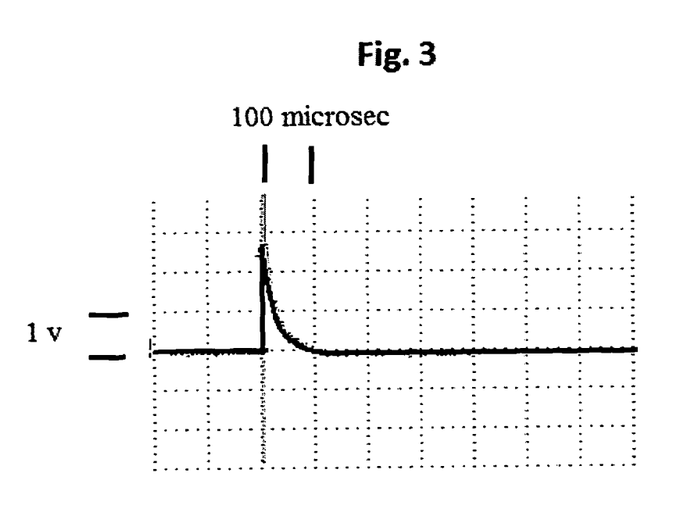
FIG. 3. Induced voltage measured by a single loop search coil 1 inch in diameter positioned 1 inch away from the surface of the pulsed magnetic field air core coil.

A magnetic stimulator was constructed using a capacitor discharge system connected to a multiple winding air core coil and xenon flash tube. This embodiment then includes magnetic field induced voltage, radiofrequency bursts, and light. The induced voltage measured 1 inch in front of the stimulating coil surface using a single loop search coil is shown in FIG. 3. The search coil is intended to estimate the maximum induced voltage so should be approximately equal to the diameter of the air core. The search coil loop can be made of insulated or bare copper wire and is positioned at the expected location of the smooth muscle to be treated. The search coil signal also contained a high frequency burst oscillation at radio frequencies (1-10 MHz) which occurred at the very start of the response shown in FIG. 3 and cannot be easily discerned in the figure since it disappears within 2 microseconds. The existence of these oscillations was verified using a 100 MHz bandwidth oscilloscope. The possible role of this high frequency oscillation is discussed later. The Xenon flash tube creates a plasma discharge which is responsible for the generation of this high frequency oscillation due to plasma resonance. Light in the UV range is also generated and its possible role is also discussed later. Note the rapid change to peak voltage followed by an exponential like return to baseline within the next approximately 100 microseconds. The magnetic stimulator was tested on isolated pig esophageal smooth muscle using an organ bath type of apparatus.

Example 1

Figure 4:
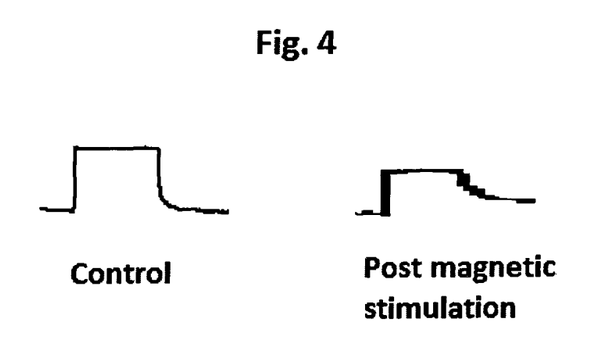
FIG. 4. Response to 50 second electrical stimulation of longitudinal smooth muscle strip tension before and following magnetic stimulation at 5 Hz.

Force responses to electrical stimulation of longitudinal esophageal smooth muscle are shown in FIG. 4 before and following magnetic stimulation. Responses are shown to electrical stimulations of about 3 volts/cm electric field using approximately a 50 second long 10 msec pulse width pulse train with a 20 Hz repetition rate. The intent was to simulate a continuous cramp contraction. Following the control measurement of FIG. 4, the muscle was stimulated by the pulse magnetic field coil with a magnetic field repetition rate of 5 Hz for 5 minutes. Following magnetic field exposure, the stimulation was repeated and the response measured as shown in the second part of FIG. 4. Note that the peak force response has significantly decreased following magnetic field exposure.

Example 2

Figure 5:
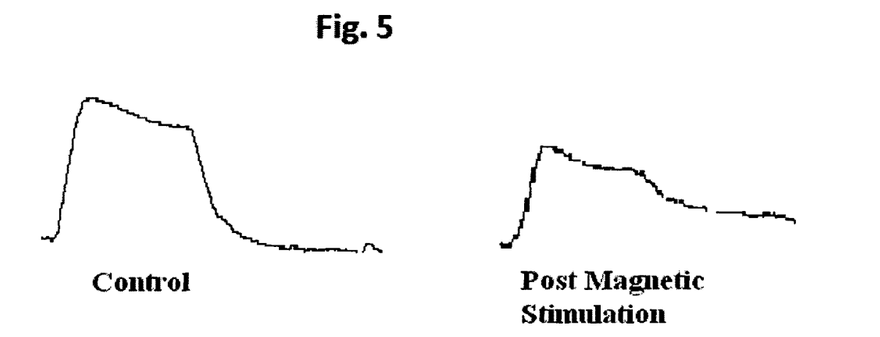
FIG. 5. Response to 50 second electrical stimulation of circular smooth muscle strip tension before and following magnetic stimulation at 5 Hz.

In FIG. 5 similar responses are shown for circular esophageal smooth muscle. For both smooth muscle types, despite the low stimulation levels used, a significant relaxation was observed to contraction following magnetic field application for about 5 minutes. Differences in responses between smooth muscle fiber types were apparent with the longitudinal showing a faster rate of rise and no overshoot. An apparent maintenance of tension due to stimulation was observed for both fiber types before final return to the original resting tension. This was interpreted as corresponding to an "off" contraction which is commonly reported for especially circular esophageal smooth muscle. The "off" contraction has been tied to release of nitric oxide. The "off" contraction response is known to be sensitive to stimulation frequency and is expected to increase at frequencies below 5 Hz(7). Thornbury 1995 reported a more than 3 fold increase in peak contraction in comparing "off" tension peak magnitudes for 4 and 1 Hz frequency. If contraction is to be promoted then a lower frequency of about 1-2 Hz would be selected as most effective according to this reference.

Example 3

Figure 6:
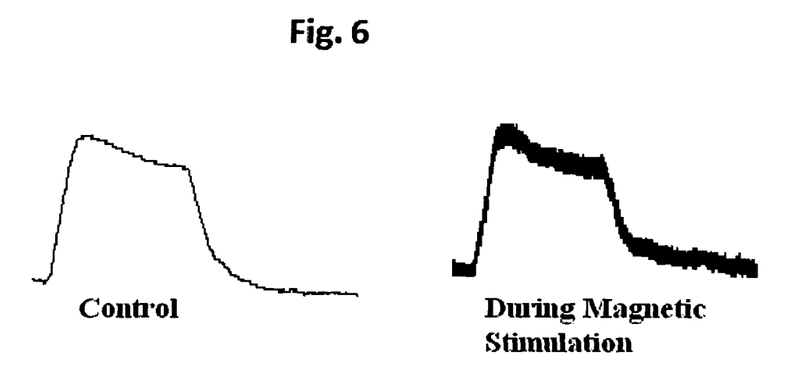
FIG. 6. Response to 50 second electrical stimulation of circular smooth muscle strip tension during magnetic stimulation at 5 Hz.
Figure 7:
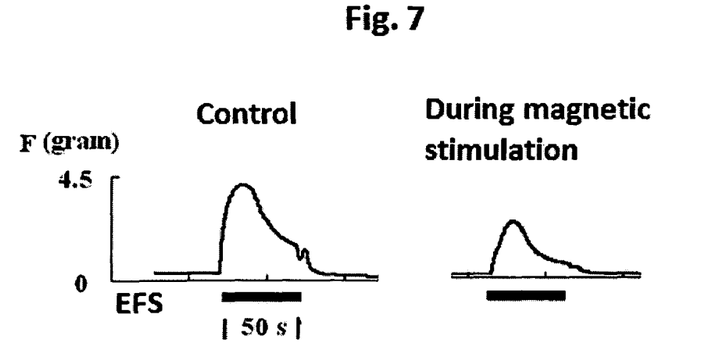
FIG. 7. Response to 50 second electrical stimulation of circular smooth muscle strip during magnetic stimulation at 10 Hz FIG. 8. Circuit diagram of pulsed magnetic field stimulator used in example.

During magnetic stimulation at 5 Hz as shown in FIG. 6, circular smooth muscle had a slightly higher peak force compared to control. This can be compared to FIG. 7 which shows the measured response to a frequency of 10 Hz which shows a significant attenuation. Note that the response during stimulation can be different than following stimulation. The lower frequency then promotes contraction and exhibits a more prominent "off" response. This is interpreted as demonstrating the effectiveness of using frequency of magnetic stimulation to promote contraction or relaxation. What is indicated is a balance which can be tipped towards relaxation or contraction by choosing the right stimulation parameters. The level of magnetic stimulation used was consistently much lower than what is known to those skilled in the art to elicit any nerve stimulation response. Thus, a direct effect on smooth muscle is possible or specific NANC nerves.

These measured responses in pig esophagus using magnetic stimulation were consistent with previously reported electrical stimulation responses of airway smooth muscle (Linden 1991) with cholinergic block applied. These examples showed the range of possibilities using magnetic stimulation. Contraction or relaxation of circular smooth muscle can be promoted using appropriate magnetic stimulation frequencies and induced voltage levels. Longitudinal smooth muscle resting tension should be similarly adjustable. Magnetic stimulation parameters such as duration, frequency, and strength can then be changed to meet the desired clinical objective. For example, for circular smooth muscle relaxation appears to be promoted for frequency of 10 Hz using magnetic stimulation as shown in FIG. 6 and contraction at a lower stimulation frequency of 5 HZ. These frequency ranges for contraction or relaxation can vary for subject to subject so adjustment will probably be necessary for optimal effect. If light flashes are used, subjects with photosensitive epilepsy must use protective coverings to avoid visual exposure. Since tension responses show "on" and "off" asymmetries, intermittent application of magnetic stimulation is another mode which can be used to enhance the net response. To promote relaxation, a continuous magnetic stimulation appears adequate, but an intermittent mode could be used to save power. A one second on followed by a one second off intermittent train has been found effective for electrical stimulation with no sacrifice in tension response and could also be effective for magnetic stimulation. For contraction, an intermittent train should be more effective due to the transient nature of the "off" contraction. Repeated stimulation of the "off" response should enhance a net contraction. The "off" response dynamics leads to an exponential decay of the order of 20-30 seconds by inspection of FIGS. 4 and 5. This justifies using an intermittent train of the order of 20=30 seconds on and 20-30 seconds off to promote a net contraction. The relatively long 20-30 second period of continuous stimulation also increases the magnitude of the "off" contraction peak (Thornbury 1995). Up to 80 seconds of continuous stimulation has been found to maximize the "off" contraction peak force. The rationale would be to allow sufficient time for recovery prior to applying another stimulus leading to another "off" response. Intermittency would also lead to halving the power requirements for this case as well if a 50/50 split is used. The duration of the applied magnetic stimulation pulse would also be expected to be a major determinant of whether contraction or relaxation results. Undesired contraction could be relaxed or excessive relaxation reversed by varying stimulation parameters.

Linden 1991 found that in airway smooth muscle a relaxed muscle contracts due to NANC stimulation. This response was observed in our experiment on circular esophageal smooth muscle during magnetic field stimulation. FIG. 6 shows the electrical response during application of magnetic stimulation. Note that the peak force was slightly larger when compared to control. Relaxation was observed following discontinuing stimulation as shown in FIG. 5. The other contraction response noted was the elevation of resting tension for some time period prior to return to original baseline in both circular and longitudinal muscles post magnetic stimulation. This is most likely what has been referred to as an "off" contraction. Comparison of FIGS. 6 and 7 confirm the prior observation(7) that frequency choice can be used to promote contraction or dilation.

DETAILED DESCRIPTION OF THE INVENTION

Figure 8:
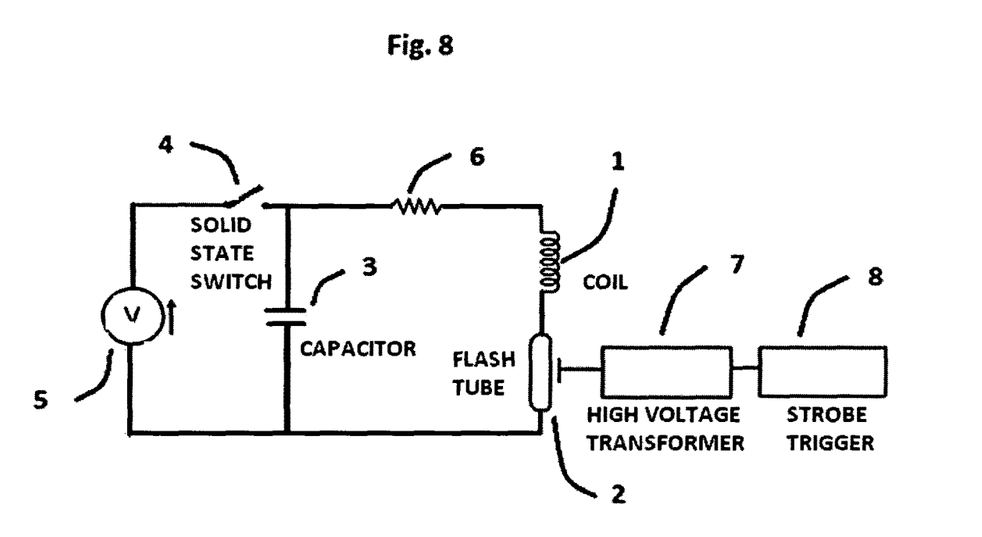

Magnetic stimulation as taught by the present inventive device relies on an asymmetric current passing through the stimulating coil. A capacitive discharge circuit with discharge into a stimulating coil 1 was used as schematically shown in FIG. 8. A Xenon flash tube 2 was used to produce a current pulse in the stimulating coil. Such a flash tube is well known to those skilled in the art to be capable of a rapid rise to peak current followed by a much slower decay. Other pulse discharge circuit designs can be used as discussed later. Capacitor 3 is intermittently charged with solid state switch 4 with a voltage source 5 and discharged when flash tube 2 is activated by strobe trigger 8 using high voltage transformer 7. Resistance 6 corresponds to coil and circuit wire resistances. The overall magnetic stimulator design result is documented by FIG. 3 which shows an induced voltage rising to a peak in a few microseconds followed by a gradual return within 100 microseconds. This difference between rising and falling times is what leads to induced current in the targeted smooth muscle. Since magnetic stimulation is repeated according to a repetition frequency, there will be a small average stimulation current which might contribute to the response because induced voltage is mainly positive as shown in FIG. 3. That the induced voltage shown in FIG. 3 was designed to have a pulse width of less than 100 microseconds was based on the minimum electrical stimulation pulse width found to successfully stimulate NANC smooth muscle receptors(5). A wider pulse width could also work, but power requirements would increase and the cholinergic nerves might be stimulated. Pulse duration was purposely set below the expected stimulation chronaxie duration (100-200 microseconds) expected for these nerves. As already mentioned, a frequency of about 5-10 HZ also promotes NANC relaxation responses according to previous electrical stimulation results. Control of this frequency is through a means of controlling the time interval between sequential pulses. These means are well known to those skilled in the art and include microprocessor control using stored software instructions or electronic timer modules using varying voltage or circuit components to vary said time interval between sequential pulses. Pulse duration can also be adjusted using microprocessor or electronic timer modules using methods also very familiar to those skilled in the art. The positive experimental results shown in the previously described example confirms the validity of these extrapolations. FIG. 10 shows the stimulating coil 1 positioned over the body region 11 containing the smooth muscle to be treated. For maximum effectiveness the coil should be placed as close as possible to the smooth muscle requiring treatment with the—polarity (negative magnetic field) positioned closest to the smooth muscle to be treated. Coil polarity in magnetic stimulation may play a role analogous to the well known effect of electrode polarity on cell membrane depolarization in electrical stimulation. Note that coil 1 in FIG. 10 has the +magnetic field indicated and the bend in handle 9 facilitates identifying this polarity. Electrical cable 10 connects to the discharge circuits of FIG. 8 or 9. In the examples the coil was positioned about 1 inch directly in front of the muscle facing the negative side. The muscle was positioned inside a glass organ bath maintained at 37 degrees C., perfused with Tyrode solution, and oxygenated(95% $O_2$, 5% $CO_2$). The muscle was kept at constant resting length and contraction force measured with a transducer.

Figure 9:
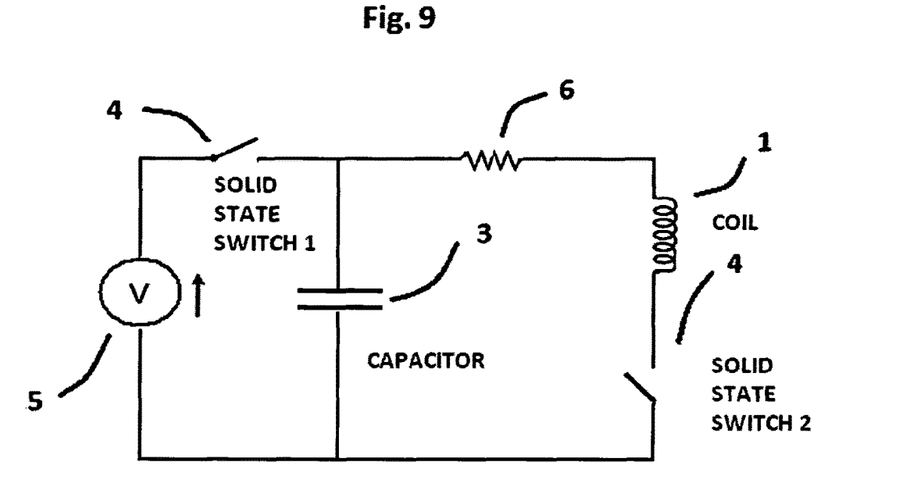
FIG. 9. Circuit diagram of alternative pulsed magnetic field stimulator.
Figure 10:
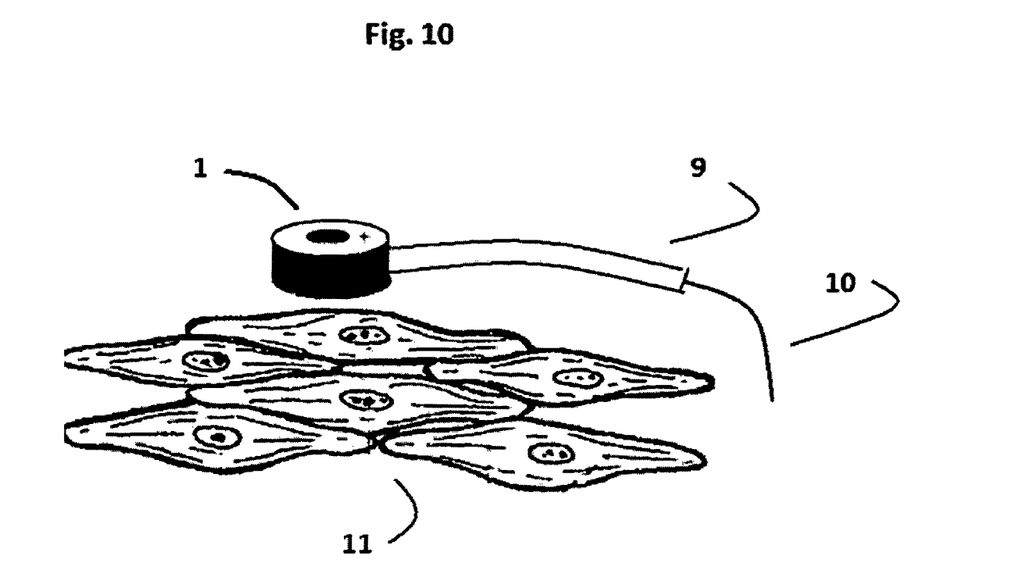
FIG. 10. Stimulating coil positioned over the smooth muscle to be treated. Note polarity indicated by bend in the handle.

In FIG. 9 an alternative circuit design or different embodiment for pulse generation is shown which can also be used and has the possible advantage of not requiring a flash lamp and light generation which may be disturbing to some. This embodiment might be advantageous when smooth muscle contraction rather than relaxation is to be promoted. The design objective would be the same to try and approximate the induced voltage of FIG. 3 by selecting the proper circuit component values. Pulse duration is then set by the choice of coil inductance and discharge capacitance. This places constraints on the stimulating coil which ideally is chosen to maximize the number of turns to produce the desired field strength. Capacitor 3 is intermittently charged by voltage source 5 using solid state switch 4 and discharged through coil 1 using another solid state switch 4. Resistance 6 corresponds to coil and circuit wire resistances. Frequency and pulse duration can be adjusted using the same methods as described earlier for FIG. 8.

Figure 11:
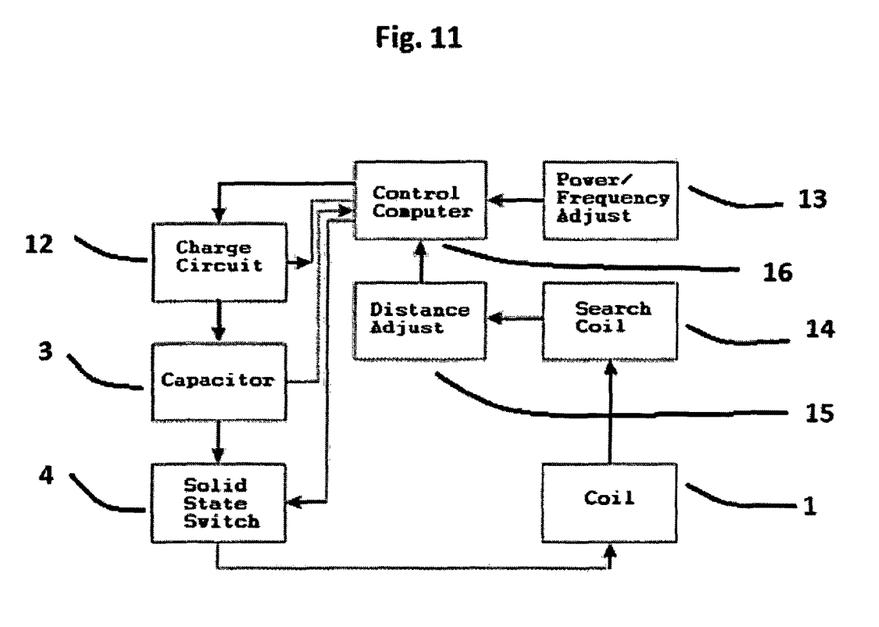
FIG. 11. Overall block diagram of inventive device.

In FIG. 11 the overall block diagram of one embodiment of the inventive device is shown. Specific features that contribute to effectiveness will now be described. Items previously covered by FIGS. 8 and 9 include charge circuit 12 components (4,5, and 3). A search coil 14 is shown which is intended to measure the induced voltage in the vicinity of the front (negative magnetic field) of the stimulating coil 1. This measurement could be useful for adjusting the level of stimulation for maximum effectiveness at the specific target area requiring treatment. The decrease of voltage as a function of distance can then be directly measured and corrected for in the initial design as well as routinely measured to insure the most effective stimulation induced voltage. Such adjustment capability corresponds to item distance adjust 15. Power level as well as frequency adjust 13 and pulse duration of stimulation as described earlier could have provision for adjustment for maximum effectiveness. Varying the distance between the stimulating coil and specific target area is another way to adjust the strength of stimulation. Intermittent operation, where magnetic stimulation is cyclically turned on and off repeatedly for different periods, is another feature which can be incorporated by a further embodiment. Control computer 16 is included in embodiments which use a dedicated microprocessor or other computer to accomplish the various adjustments and information displays of settings like frequency, targeted distance, and power level. FIG. 10 shows an air core coil of conventional multiple winding circular shape. Coils can have different shapes like rectangular or oval which might be more convenient for application to certain parts of the body and still function as described above in different embodiments. Coils can even be made wound on a flat surface and applied with or without an adhesive layer for positioning over a specific part of the body. The adhesive layer could be put on a disposable coil cover with the adhesive layer facing the body surface to be treated or directly on one coil surface. Disposability of coils and/or cover is another embodiment to minimize contamination for use on different patients. Multiple coils connected in series or parallel are another possible embodiment which would permit simultaneous treatment of different body areas at the same time. Adjustment of strength of stimulation is important to insure the stimulation of a targeted body region. Instead of an adjustment located within the magnetic stimulator electronics as shown in FIG. 11, in another embodiment adjustment of this strength can also be accomplished by fitting coils of different sizes and number of coil windings which can be changed using an electrical connector.

Yamashiro(U.S. Pat. No. 6,520,903) has taught use of a magnetic field stimulating coil and light for energy stimulation of the body. Light stimulation of areas near the skin surface such as acupuncture points is possible with this method, but especially in the ultraviolet range penetration of light may be limited to less than a centimeter. Thus, organs such as the stomach or lungs may only be primarily reached by magnetic stimulation which must be specifically adjusted for smooth muscle contraction modulation as indicated earlier or by high frequencies present in the xenon strobe discharge as discussed later. The combined use of magnetic field and light may in another embodiment also promote deeper penetration due to the known ability of a magnetic field to focus the electromagnetic emissions of a plasma discharge. If this occurs, then uv light is known to promote release of nitric oxide which is a well known to those skilled in the art as a smooth muscle dilator (Furchgott 1961).

Another characteristic of a plasma discharge system such as shown in FIG. 8 for a Xenon flash tube is plasma resonance frequency. The resonance frequency is a function of the specific flash tube and can be selected for resonance in the range 1-10 MHz. The importance of this high frequency component has been established by prior studies by Miura (1991) who showed that frog smooth muscle dilation was promoted by 1-10 MZ bursts 100 microseconds in duration. Their results showed that nitric oxide was the agent responsible. Our experimental results showing pig smooth muscle relaxation was collected using 1-10 MHz bursts of duration 100 microseconds which suggested that a similar mechanism may hold in mammals.

There are then at least three separate physiological mechanisms which promote relaxation of smooth muscle by embodiments of the present inventive device. (1) Magnetically induced current of the appropriate magnitude and frequency possibly tied to mainly ATP release (2) radiofrequency (1-10 Mz) plasma resonance bursts less than 2 microseconds in duration possibly tied to nitric oxide release and (3) Pulsed light in the uv range focused by the simultaneous magnetic field also tied to nitric oxide release. While nitric oxide release is probably limited to skin due to limited depth of penetration, blood and hemoglobin from skin circulation could carry the effect of nitric oxide deeper into tissue. All three in combination would be the most effective, but any combination of one or more could be used. Prior methods have mainly applied mechanism (1). Contraction of smooth muscle has been mainly promoted in the prior art by stimulating nerves connected to smooth muscle. In contrast, by limiting the level of induced voltage below the threshold of neural stimul;ation and proper choice of pulse duration and frequency the current inventive device has experimentally demonstrated the possibility of promoting contraction of smooth muscle. The preferred embodiment for contraction would be magnetic field stimulation alone, since radiofrequency bursts and light both primarily promote relaxation even though a nitric oxide role in contraction has been demonstrated. Other embodiments could exploit this possible role.

REFERENCES

The following references are incorporated herein by reference:

1. Hungin, A., L. Chang, G. Locke, E. Dennis, and V. Barghout. Irritable bowel syndrome in the United States: prevalence, symptom patterns, and impact. AlimentPharmacolTher, 21: 1365-1375, 2005.

2. Lacy, B., K. Weisser, and R. De Lee. The treatment of irritable bowel syndrome., TherapAdvGastroenterol , 2: 221-238, 2009.

3. Linden, A., A. Ullman, G. Lofdahl, and B. Shoogh. Non-adrenergic, non-cholinergic neural activation stabilizes smooth-muscle tone independently of eicosanoid factors in guinea-pig isolated airways. Br J Pharmacol, 104: 509-513, 1991.

4. Hoffinann, T., S. Mendez, P. Staats, C. Emala, and P. Guo. Inhibition of histamine-induced bronchoconstriction in guinea pig and swine by pulsed electrical vagus nerve stimulation. Neuromodulation, 12: 261-269, 2009.

5. Ellis, J, and B. Undem. Non-adrenergic, non-cholinergic contractions in the electrically field stimulated guinea-pig trachea, Br J Pharmacol, 101: 875-880, 1990.

6. Grishin, S., A. Tepov, et al., Different effects of ATP on the contractile activity of mice diaphragmatic and skeletal muscle, 49: 756-763, 2006.

7. Thornbury, K., K. Donaghy, and J. Peake. Contractions of the NANC post-stimulus ('rebound') contraction of the urinary bladder neck muscle in sheep. Br J Pharmacol, 116: 2451-2456, 1995.

8. Furchgott, R., S. Ehrreich, and E. Greenblatt. The photoactivated relaxation of smooth muscle of rabbit aorta. J. Gen. Physiol. 44: 499-519, 1961.

9. Miura, M. and J. Okada. Non-thermal vasodilation by radiofrequency burst-type electromagnetic field radiation in the frog. J. Physiol. 435: 257-273, 1991.

I claim:

1. A method of modulating contraction force of non-cholinergic receptor containing muscle in a subject in need thereof, comprising: generating monopolar magnetic field pulses, each pulse having a leading edge phase which rises or falls to a maximum or a minimum magnetic field level in less time than the trailing edge phase where the pulse returns to the baseline level; decreasing said contraction force while minimizing cholinergic mediated said contraction force responses via said monopolar magnetic field pulses; and a plurality of pulses being generated at a pulse repetition frequency; adjusting said pulse repetition frequency between 5 Hz to 10 Hz until contraction force is decreased ; duration of each pulse having a range from 0.1 microseconds to 100 microseconds; magnitude of electric field induced by said magnetic field on said non-cholinergic receptor containing muscle having a range from 0.1 volts per centimeter to 3 volts per centimeter.

2. The method of claim 1, wherein said generating monopolar magnetic field pulses comprises generating monopolar magnetic field pulses using one or more coils adapted for placement over or in the proximate region to the muscle of the subject to be treated.

* * * * *